US009615645B2

(12) United States Patent
Yiu

(10) Patent No.: US 9,615,645 B2
(45) Date of Patent: Apr. 11, 2017

(54) ADJUSTABLE ROLLER AND COSMETIC DEVICE

(71) Applicant: SOFT LINES INTERNATIONAL, LTD., Kowloon (HK)

(72) Inventor: Wai Wah Yiu, Kowloon (HK)

(73) Assignee: SOFT LINES INTERNATIONAL, LTD., Kowloon (HK)

( * ) Notice: Subject to any disclaimer, the term of this patent is extended or adjusted under 35 U.S.C. 154(b) by 20 days.

(21) Appl. No.: 14/832,957

(22) Filed: Aug. 21, 2015

(65) Prior Publication Data

US 2016/0295988 A1   Oct. 13, 2016

Related U.S. Application Data

(60) Provisional application No. 62/145,801, filed on Apr. 10, 2015.

(51) Int. Cl.
| | | |
|---|---|---|
| *A45D 29/05* | (2006.01) | |
| *F16H 19/04* | (2006.01) | |
| *A45D 29/14* | (2006.01) | |
| *A61B 17/54* | (2006.01) | |

(Continued)

(52) U.S. Cl.
CPC .............. *A45D 29/05* (2013.01); *A45D 29/14* (2013.01); *A61B 17/54* (2013.01); *F16H 19/04* (2013.01); *A61B 2017/00398* (2013.01); *A61B 2017/00473* (2013.01); *A61B 2017/00477* (2013.01); *A61B 2017/00734* (2013.01); *A61B 2017/00747* (2013.01); *A61B 2017/00761* (2013.01); *A61B 2017/320004* (2013.01)

(58) Field of Classification Search
CPC ...... A45D 29/007; A45D 29/04; A45D 29/05; A45D 29/14; A45D 29/12; A61B 17/54; A61B 2017/320004; A61B 2017/320008; A61B 5/04025; B23D 51/12; B23D 71/00; B23D 71/005; F16H 19/04
USPC .............. 132/73.6, 75.8, 76.4, 76.5; 606/131
See application file for complete search history.

(56) References Cited

U.S. PATENT DOCUMENTS 702,170 A * 6/1902 Allison ................... A45D 29/11
132/76.5
1,482,837 A * 2/1924 Buck ...................... A45D 29/14
132/75.8

(Continued)

FOREIGN PATENT DOCUMENTS

| CN | 2489038 | 5/2002 |
|---|---|---|
| CN | 1768641 | 5/2006 |

(Continued)

OTHER PUBLICATIONS

International Search Report and Written Opinion for PCT Application No. PCT/IB2015/056355, mail date Jan. 18, 2016, 9 pages.

*Primary Examiner* — Todd E Manahan
*Assistant Examiner* — Jennifer Gill
(74) *Attorney, Agent, or Firm* — Foley & Lardner LLP

(57) ABSTRACT

A roller assembly for a cosmetic device includes a cylindrical drum portion having an interior and an abrasive outer surface; first and second ends enclosing opposite ends of the cylindrical drum portion; and first and second posts extending from the interior of the cylindrical drum portion and being movable along a longitudinal axis of the roller assembly.

15 Claims, 5 Drawing Sheets

(51) Int. Cl.
 *A61B 17/00* (2006.01)
 *A61B 17/32* (2006.01)

(56) References Cited

U.S. PATENT DOCUMENTS

| | | | | | |
|---|---|---|---|---|---|
| 1,829,338 | A | * | 10/1931 | Bynum | A61B 17/54 |
| | | | | | 132/76.5 |
| 5,137,173 | A | * | 8/1992 | Hughes | A47K 10/424 |
| | | | | | 221/154 |
| 5,640,979 | A | * | 6/1997 | Trenary | A45D 29/17 |
| | | | | | 132/73 |
| 5,864,921 | A | * | 2/1999 | Chou | A45C 13/262 |
| | | | | | 16/405 |
| 6,076,984 | A | * | 6/2000 | Legrain | A45D 40/261 |
| | | | | | 401/1 |
| 6,170,122 | B1 | * | 1/2001 | Kuo | A45C 13/262 |
| | | | | | 16/405 |
| 6,391,034 | B1 | * | 5/2002 | Adamson | A61B 17/54 |
| | | | | | 606/131 |
| 8,551,117 | B2 | | 10/2013 | Yiu | |
| 2002/0107527 | A1 | * | 8/2002 | Burres | A45D 29/14 |
| | | | | | 606/131 |
| 2011/0257588 | A1 | * | 10/2011 | Knowlton | A61B 17/322 |
| | | | | | 604/22 |
| 2013/0056016 | A1 | * | 3/2013 | Guay | A45D 34/041 |
| | | | | | 132/200 |
| 2013/0081645 | A1 | * | 4/2013 | Caviness | A45D 29/00 |
| | | | | | 132/75.8 |
| 2014/0025091 | A1 | * | 1/2014 | Yiu | A61B 17/54 |
| | | | | | 606/131 |
| 2015/0226292 | A1 | * | 8/2015 | Sokolofsky | F16H 19/04 |
| | | | | | 74/109 |

FOREIGN PATENT DOCUMENTS

| | | |
|---|---|---|
| CN | 2784529 | 5/2006 |
| CN | 104355079 | 2/2015 |
| GB | 0 381 130 | 9/1932 |
| WO | WO-01/39716 | 6/2001 |
| WO | WO2014118577 * | 8/2014 |

* cited by examiner

SECTION A-A

SECTION B-B

ADJUSTABLE ROLLER AND COSMETIC DEVICE

CROSS REFERENCE TO RELATED APPLICATIONS

This application claims the benefit of U.S. Provisional Application No. 62/145,801, filed Apr. 10, 2015, which is incorporated herein by reference in its entirety.

BACKGROUND

The present disclosure relates generally to the field of rollers such as those used to abrade, smooth, polish, remove material from, etc., surfaces such as skin, nails, and the like.

SUMMARY

One embodiment relates to a roller assembly for a cosmetic device, comprising a cylindrical drum portion having an interior and an abrasive outer surface; first and second ends enclosing opposite ends of the cylindrical drum portion; and first and second posts extending from the interior of the cylindrical drum portion and being movable along a longitudinal axis of the roller assembly.

Another embodiment relates to a cosmetic device, comprising a housing defining first and second cavities and having a drive system disposed therein; and a roller assembly including a cylindrical drum portion having an interior and an abrasive outer surface; first and second ends enclosing opposite ends of the cylindrical drum portion; and first and second posts extending from the interior of the cylindrical drum portion and being movable along a longitudinal axis of the roller assembly; wherein the first and second posts are removably received within the first and second cavities in the housing such that the drive system is configured to rotate the roller.

Another embodiment relates to a roller assembly, comprising a cylindrical drum including a first drum portion coupled to a second drum portion, the cylindrical drum defining a longitudinal axis; first and second end portions coupled to opposite ends of the cylindrical drum; first and second posts extending through the first and second end portions, respectively, wherein the first and second posts are rotational fixed relative to the first and second drum portions, and wherein the first and second posts are movable along the longitudinal axis; a gear; and a spring member; wherein the first and second posts extend from first and second adjustment members, respectively, and wherein the first and second adjustment members engage the gear such that movement of one of the first and second posts causes movement of the other of the first and second posts in an opposite direction; and wherein the spring member engages at least one of the first and second adjustment members such that the first and second posts are biased away from each other.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
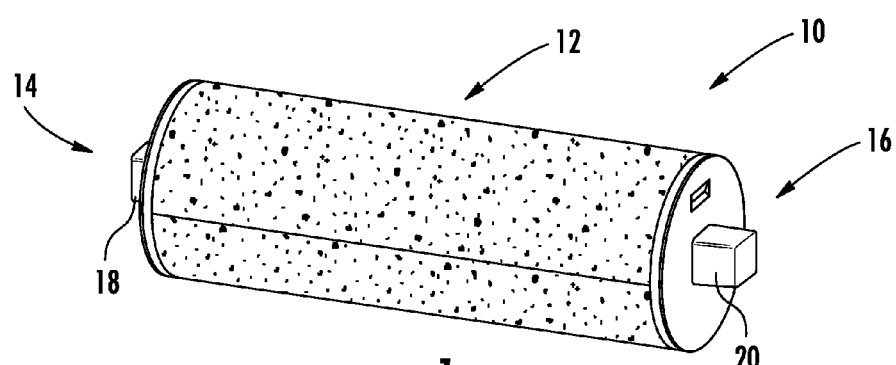
FIG. 1 is a perspective view of a roller assembly according to one embodiment.
Figure 2:
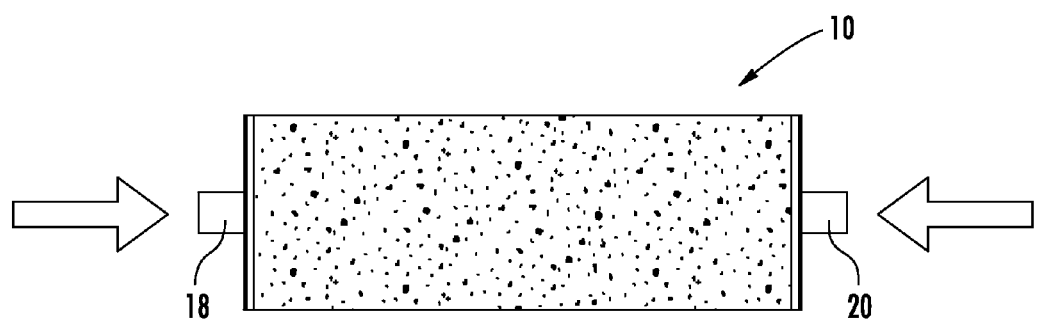
FIG. 2 is a side view of the roller assembly of FIG. 1 according to one embodiment.
Figure 3:
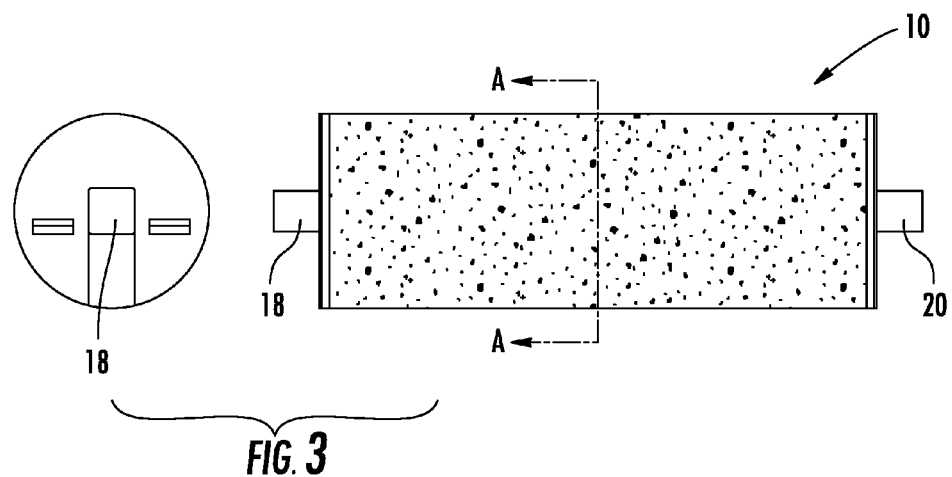
FIG. 3 is a another side view and an end view of the roller assembly of FIG. 1 according to an exemplary embodiment.
Figure 4:
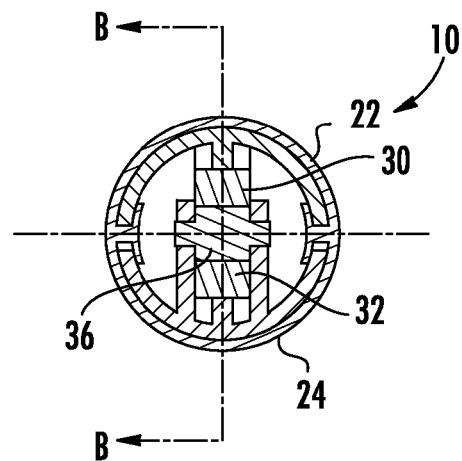
FIG. 4 is a sectional view of the roller assembly of FIG. 1 taken along line A-A in FIG. 3 according to one embodiment.

In the following detailed description, reference is made to the accompanying drawings, which form a part thereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Referring to the figures generally, various embodiments disclosed herein relate to an adjustable roller and/or devices that utilize adjustable rollers. The roller may be usable to remove material from, abrade, smooth, polish, or otherwise act on a surface such as skin, nails, etc. As discussed in greater detail herein, the adjustable roller may be used in a wide variety of applications, including pedicures, manicures, exfoliation, and the like. In some embodiments, the adjustable roller provides an easy and reliable way to insert and remove the roller assembly to and from a cosmetic device.

Referring to FIGS. 1-7, roller assembly 10 is shown according to one embodiment. Roller assembly 10 is generally a cylindrical member configured to be used in connection with a cosmetic or other device such that during use, roller assembly 10 rotates about its longitudinal axis. In one embodiment, roller assembly 10 includes a cylindrical portion 12 and first and second end portions 14, 16 provided at opposite ends of cylindrical portion 12. A first drive member or post 18 extends beyond first end portion 14 and a second drive member or post 20 extends beyond second end portion 16. Drive members 18, 20 (e.g., posts, shafts, projections, etc.) are shown as being generally rectangular in shape, although according to various alternative embodiments, drive members 18, 20 may take other forms (e.g., keyed, splined, T-shaped, cross-shaped, irregularly-shaped, etc.). As discussed in greater detail below, drive members 18, 20 provide an adjustable roller in that drive members 18, 20 are movable into and out of cylindrical portion 12 to enable insertion and removal of roller assembly 10 into and out of a cosmetic or other device.

Referring to FIGS. 4-7, various components of roller assembly 10 are shown in greater detail according to one embodiment. Roller assembly 10 includes a first abrasive member 22 and a second abrasive member 24. Abrasive members 22, 24 are disposed over first and second body portions 26, 28. First and second body portions 26, 28 are coupled together to define an interior of roller assembly 10.

Within the interior of roller assembly 10, first and second adjustment members 30, 32 translate relative to one another to provide for the adjustability of drive members 18, 20 (which are provided on adjustment members 30, 32, respectively). A spring 34 and gear or pinion 36 interact with first and second adjustment members 30, 32 to provide equal translation of the components in opposing directions.

Abrasive members 22, 24 are generally semi-cylindrical in shape (covering one side of a cylinder each) and collectively form a cylindrical abrasive surface. Abrasive members 22, 24 are provided to the outside surfaces of first and second body portions 26, 28, respectively. In one embodiment, the longitudinal edges of abrasive members 22, 24 are tucked into a gap between first and second body portions 26, 28 to retain abrasive members 22, 24. In other embodiments, abrasive members may alternatively or additionally be held in place via other means, including mechanical fasteners, adhesives, friction fits, and the like. In yet further embodiments, abrasive members 22, 24 may be omitted and an abrasive surface may be sprayed, brushed, or otherwise applied to form an abrasive surface about all or a portion of first and second body portions 26, 28. Abrasive members 22, 24 may include particles configured to remove material (e.g., skin, nails, etc.) through rotation of roller assembly 10.

First body portion 26 includes a semi-cylindrical body 38 extending from a first end 40 to a second end 46. First end 40 includes a pair of recesses 42 and an aperture 44. Recesses 42 are configured to receive projections 56, 58 on second body portion 28. Aperture 44 is configured to receive first drive member 18 and enable translational movement of first drive member 18 along the longitudinal axis of roller assembly 10. Second end 46 includes a projection 48 configured to engage a recess 62 provided on second body portion 28. First body portion 26 further includes first and second pins 50, 52. Pins 50, 52 are in some embodiments configured to engage corresponding bores 68, 72 in posts 66, 70 provided on second body portion 28.

Second body portion 28 includes a semi-cylindrical body 54 extending from a first end 56 to a second end 60. First end 56 includes projections 58 configured to engage recesses 42 on first body portion 26. Second end 60 includes a recess 62 and an aperture 64. Recess 62 is configured to receive projection 48 on first body portion 26. Aperture 64 is configured to receive second drive member 20 and enable translational movement of second drive member 20 along the longitudinal axis of roller assembly 10. Second body portion 28 further includes posts 66, 70 having bores 68, 72, respectively, which are configured to receive pins 50, 52 on first body portion 26. Second body portion 28 also includes a gear support 74. Support 74 supports gear 36 within roller assembly 10.

Figure 6:
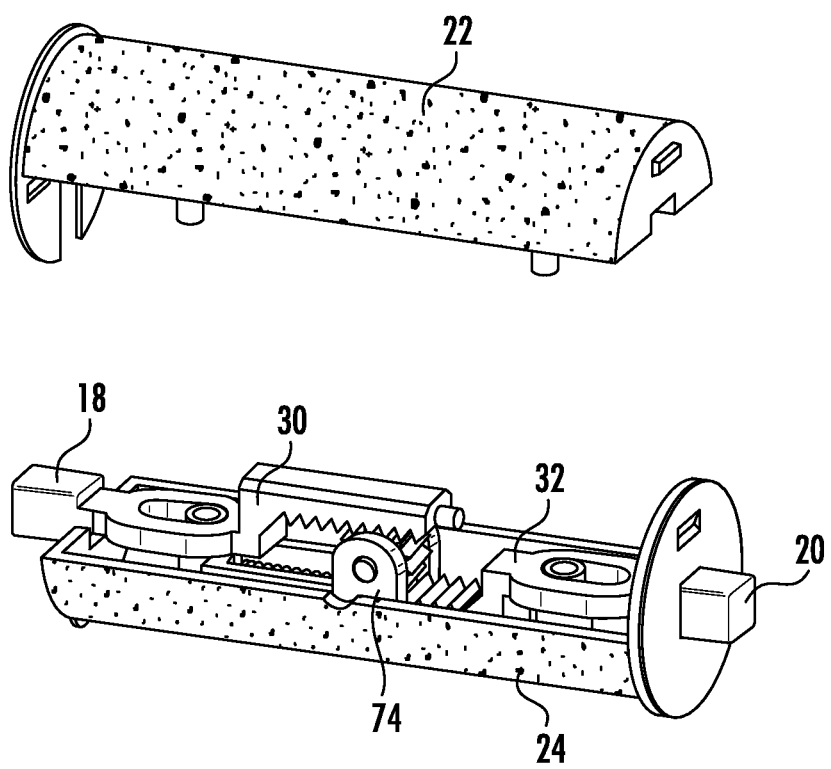
FIG. 6 is a partially exploded view of the roller assembly of FIG. 1 according to one embodiment.
Figure 7:
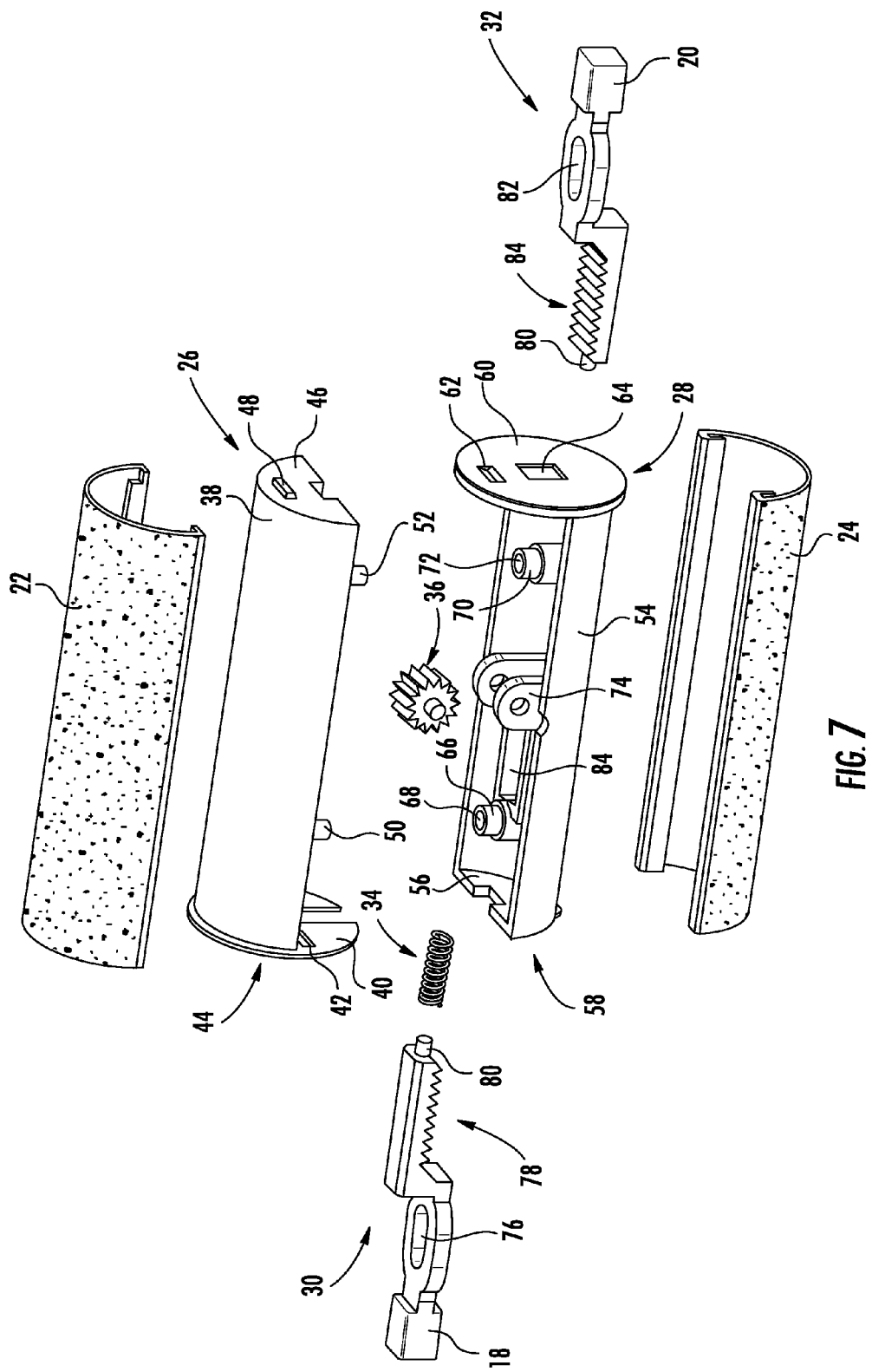
FIG. 7 is an exploded view of the roller assembly of FIG. 1 according to one embodiment.

As shown in FIGS. 6 and 7, first body portion 26 and second body portion 28 are configured to be coupled together by engaging projections 58 with recesses 42 on the first end of roller assembly 10, and by engaging projection 48 with recess 62 on a second end of roller assembly 10. Pins 50, 52 and bores 68, 72 further serve to align first and second body portions 26, 28 during assembly of roller assembly 10. It shall be noted that according to various alternative embodiments, the relative positions of the projections/recesses and/or pins/posts may be reversed, and varying numbers of such components and varying locations may be used.

First and second adjustment members 30, 32, spring 34, and gear 36 collectively provide an adjustment mechanism for roller assembly 10. By pressing drive members 18, 20 inward and toward each other, first and second adjustment members 30, 32 translate relative to each other to reduce the distance between the outermost ends of drive members 18, 20, thereby enabling easy insertion and removal of roller assembly 10.

First adjustment member 30 includes first drive member 18, first adjustment aperture 76, first adjustment rack 78, and spring mount 80. First drive member 18 is configured to be received by a drive system of a cosmetic device, such that rotation of first drive member 18 results in a corresponding rotation of roller assembly 10. In other embodiments, drive member 18 is not driven, but acts as a support shaft or pin for roller assembly 10. First adjustment aperture 76 receives pin 50 to limit the translational movement of first drive member 18. Rack 78 includes a number of gear teeth that mesh with corresponding gear teeth on gear 36 to form a rack and pinion type adjustment feature.

Second adjustment member 32 includes second drive member 20, second adjustment aperture 82, second adjustment rack 84, and spring mount or pin 80. Second drive member 20 is configured to be received by a drive system of a cosmetic device, such that rotation of second drive member 20 results in a corresponding rotation of roller assembly 10. In other embodiments, drive member 20 is not driven, but acts as a support shaft or pin for roller assembly 10. Second adjustment aperture 82 receives pin 52 to limit the translational movement of second drive member 20. Rack 84 includes a number of gear teeth that mesh with corresponding gear teeth on gear 36 to form a rack and pinion type adjustment feature. One or both of spring mounts 80 are configured to receive spring 34 such that second adjustment member 32, and by way of gear 36, first adjustment member 30, are biased away from each other. As such, in one embodiment, first and second drive members 18, 20 are biased away from each other toward a fully extended position. It should be noted that according to various alternative embodiments, springs may be mounted on one or both of first adjustment member 30 and second adjustment member 32 to provide a desired outward biasing force for adjustment members 30, 32.

As shown in FIG. 6, in one embodiment, due to the meshing of the gear teeth on racks 78, 84 with the gear teeth on gear 36, first and second drive members 18, 20 move equal distances into and out of the interior of roller assembly 10. Furthermore, should a user press on only one of drive members 18, 20, both drive members will move inward an equal distance.

Figure 5:
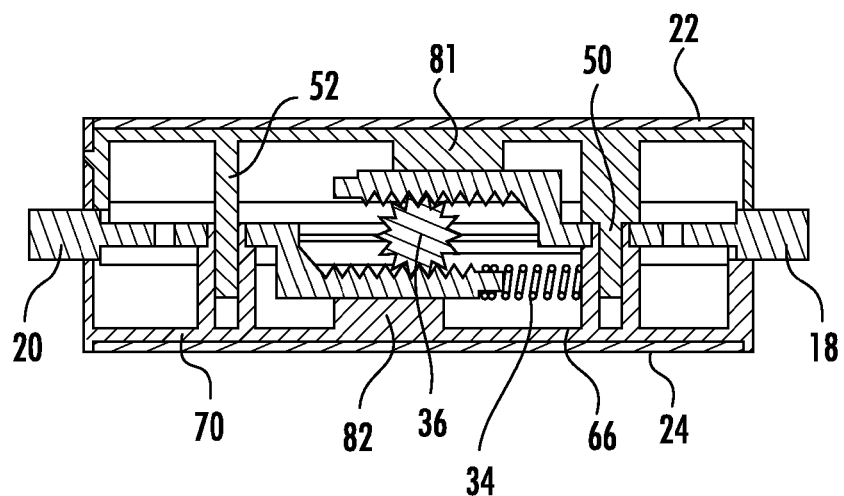
FIG. 5 is a sectional view of the roller assembly of FIG. 1 taken along line B-B in FIG. 4 according to one embodiment.

Referring further to FIGS. 5 and 6, the interaction of spring 34 and gear 36 with first and second adjustment members 30, 32 is shown in greater detail according to one embodiment. Spring 34 may be a coil spring and be configured to bias second adjustment member 32 in an outward direction (e.g., such that drive members 18, 20 are biased away from each other). In one embodiment, post 66 includes a spring retaining member (e.g., a boss, projection, etc.) configured to maintain spring 34 in a proper position. Furthermore, in some embodiments, a spring guide 84 extends along the lateral sides of spring 34 to prevent lateral deflection of spring 34 during use.

Gear 36 is a circular gear having teeth extending about its exterior surface. Gear 36 is mounted on gear support 74 in a rotatable fashion and is positioned to engage adjustment racks 78, 84 on first and second adjustment members 30, 32, respectively. As shown in FIG. 5, in one embodiment first body portion 26 includes a first rack guide 81 and second body portion 28 includes a second rack guide 82. Rack guides 81, 82 are configured to prevent deflection of adjustment racks 78, 84 away from gear 36 during use. In some embodiments, rack guides 81, 82 define a substantially flat surface configured to slidingly engage the back surfaces of adjustment members 30, 32 (e.g., the surfaces opposite racks 78, 84). In other embodiments, rack guides 81, 82 are spaced apart from adjustment members 30, 32 to permit a predetermined amount of deflection.

To assemble roller assembly, 10, first and second adjustment members 30, 32 are positioned within second body portion 28 such that spring 34 is mounted on spring mount 80 and gear 36 is disposed between adjustment racks 78, 84. Drive members 18, 20 are positioned to extend out opposite ends of second body portion 28. First body portion 26 is then aligned with second body portion 28 such that pins 50, 52 are aligned with bores 68, 72. First body portion 26 is then coupled to second body portion 28 by engagement of projections 58 with recesses 42 and by engagement of projection 48 with recess 62. Once the components are coupled together, first and second drive members 18, 20 are movable in an adjustable fashion to enable easy insertion and removal of roller assembly 10.

Figure 8:
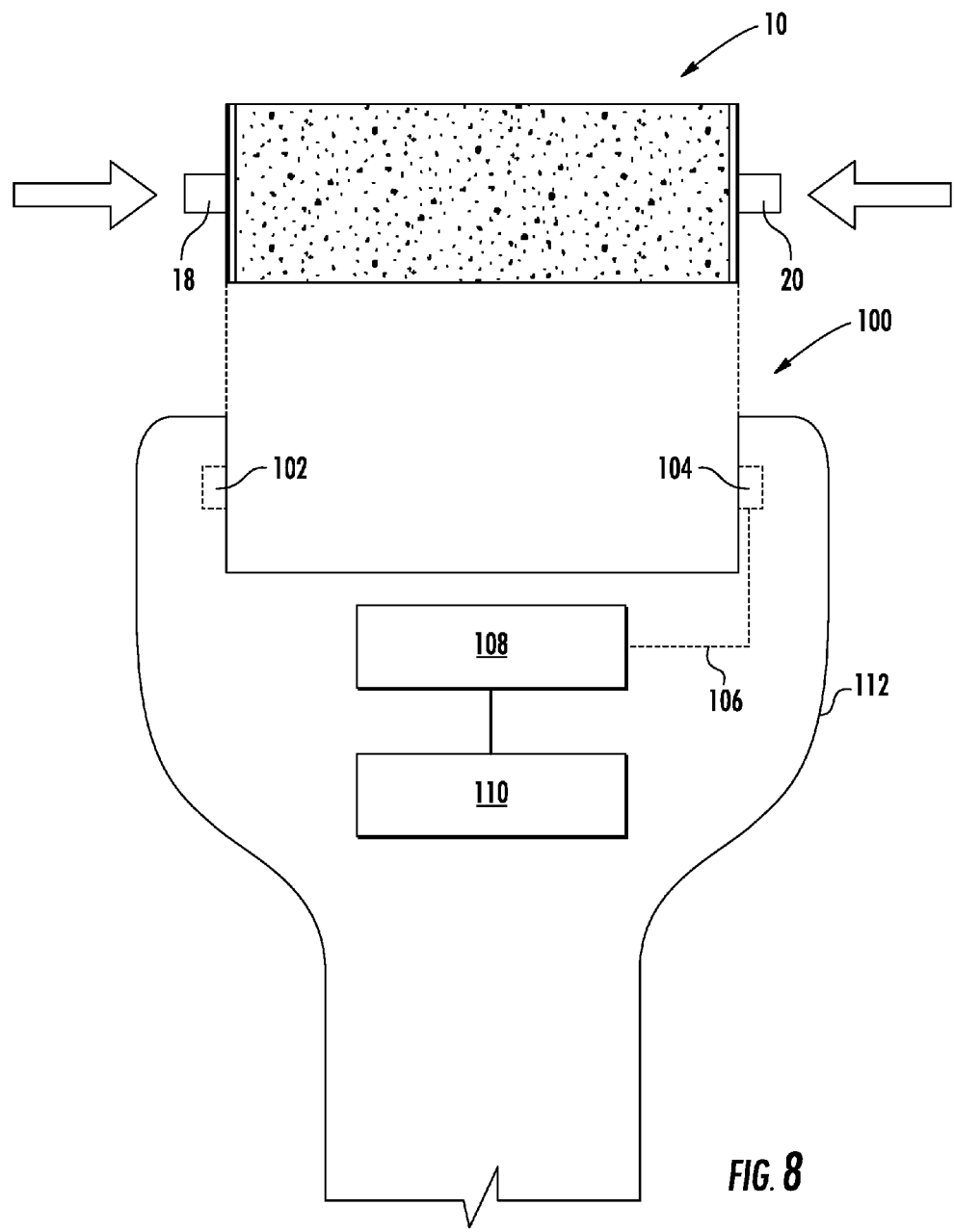
FIG. 8 is an illustration of the roller assembly of FIG. 1 and a cosmetic or other device according to one embodiment.

Referring now to FIG. 8, to insert or install roller assembly 10 into a device such as device 100, a user presses drive members 18, 20 toward each other. With drive members 18, 20 in a depressed position, roller assembly 10 may be inserted into a proper position within device 100, such that drive members 18, 20 engage corresponding cavities 102, 104 (e.g., recesses, etc.) in device 100. In one embodiment, device 100 is a cosmetic device having an electromechanical drive system configured to rotate roller assembly 10. For example, in one embodiment, device 100 includes a drive member 106 (e.g., a gear, belt, etc.) coupled to a drive mechanism 108 (e.g., an electric motor, etc.), which is in turn coupled to a power source 110 (e.g., a battery, a power connector, etc.). The various components of device 100 may be provided within housing 112. Device 100 may include a wide range of cosmetic or other devices according to various alternative embodiments.

It should be noted that in various alternative components, the various components of roller assembly 10 and device 100 may be made of any suitable materials, including polymers (e.g., plastic, rubber, etc.), metals (e.g., aluminum, etc.), composites, or combinations thereof. Other materials may be used according to various alternative embodiments.

Although the figures may show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A roller assembly for a cosmetic device, comprising:
   a cylindrical drum portion having an interior and an abrasive outer surface;
   first and second ends enclosing opposite ends of the cylindrical drum portion;
   a first adjustment member disposed within the interior and having a first plurality of gear teeth and a first post extending through the first end of the drum portion;
   a second adjustment member disposed within the interior and having a second plurality of gear teeth and a second post extending through the second end of the drum portion; and
   a gear having a third plurality of gear teeth configured to engage the first plurality of gear teeth on the first adjustment member and the second plurality of gear teeth on the second adjustment member such that the first and second posts are movable relative to the drum portion along a longitudinal axis of the roller assembly.

2. The assembly of claim 1, wherein the abrasive outer surface is provided by a pair of abrasive members.

3. The assembly of claim 1, wherein rotation of the first and second posts causes a corresponding rotation of the drum portion.

4. The assembly of claim 1, further comprising a spring coupled to at least one of the first adjustment member and the second adjustment member and configured to bias the first and second posts away from each other.

5. The assembly of claim 1, further comprising first and second pins coupled to the cylindrical drum portion and configured to engage adjustment apertures in the first and second adjustment members to limit travel of the first and second adjustment members.

6. The assembly of claim 1, wherein the drum portion includes first and second portions configured to be coupled together in a snap-fit fashion.

7. The assembly of claim 1, wherein the first and second posts are rectangular in shape.

8. A cosmetic device comprising:
   a housing defining first and second cavities and having a drive system disposed therein for driving a roller assembly; and
   the roller assembly including:
     a cylindrical drum portion having an interior and an abrasive outer surface;
     first and second ends enclosing opposite ends of the drum portion; and
     a first adjustment member disposed within the interior and having a first plurality of gear teeth and a first post extending through the first end of the drum portion;
     a second adjustment member disposed within the interior and having a second plurality of gear teeth and a second post extending through the second end of the drum portion; and
     a gear having a third plurality of gear teeth configured to engage the first plurality of gear teeth on the first adjustment member and the second plurality of gear teeth on the second adjustment member such that the first and second posts are movable relative to the drum portion along a longitudinal axis of the roller assembly;
   wherein the first and second posts are removably received within the first and second cavities in the housing such that the drive system is configured to rotate the roller.

9. The device of claim 8, wherein the abrasive outer surface is provided by a pair of abrasive members.

10. The device of claim 8, wherein movement of one of the first and second adjustment members causes a corresponding movement of the other of the first and second adjustment members.

11. The device of claim 8, further comprising a spring coupled to at least one of the first adjustment member and the second adjustment member and configured to bias the first and second posts away from each other.

12. The device of claim 8, further comprising first and second pins coupled to the cylindrical drum portion and configured to engage adjustment apertures in the first and second adjustment members to limit travel of the first and second adjustment members.

13. The device of claim 8, wherein the drum portion includes first and second portions configured to be coupled together in a snap-fit fashion.

14. The device of claim 8, wherein the first and second posts are rectangular in shape.

15. A roller assembly, comprising:
- a cylindrical drum including a first drum portion coupled to a second drum portion, the cylindrical drum defining a longitudinal axis;
- first and second end portions provided at opposite ends of the cylindrical drum;
- first and second posts extending through the first and second end portions, respectively, wherein the first and second posts are rotationally fixed relative to the first and second drum portions, and wherein the first and second posts are movable along the longitudinal axis;
- a gear; and
- a spring member;
- wherein the first and second posts extend from first and second adjustment members housed within the drum, respectively, and wherein the first and second adjustment members each include a plurality of gear teeth that engage a plurality of gear teeth on the gear such that movement of one of the first and second posts causes movement of the other of the first and second posts in an opposite direction; and
- wherein the spring member engages at least one of the first and second adjustment members such that the first and second posts are biased away from each other.

\* \* \* \* \*